United States Patent [19]

Sher

[11] Patent Number: 4,483,348
[45] Date of Patent: Nov. 20, 1984

[54] SKIN TESTING DEVICE

[76] Inventor: Nathan Sher, 11 Caldy Ct., Willowdale, Ontario, Canada, M2L 2J5

[21] Appl. No.: 361,367

[22] Filed: Mar. 25, 1982

[51] Int. Cl.³ .............................................. A61B 10/00
[52] U.S. Cl. .................................... 128/743; 128/333; 604/290
[58] Field of Search ................... 128/743, 329 R, 333; 30/319, 365; 604/289–290

[56] References Cited

U.S. PATENT DOCUMENTS

| | | | |
|---|---|---|---|
| 1,619,424 | 3/1927 | Latagliata | 128/329 |
| 2,522,309 | 9/1950 | Simon | 128/743 |
| 3,074,395 | 1/1963 | Kevorkian | 30/365 |
| 3,289,670 | 12/1966 | Krug et al. | 128/743 |
| 3,556,080 | 1/1971 | Hein | 128/743 |
| 4,237,906 | 12/1980 | Havstad et al. | 128/743 |
| 4,270,548 | 6/1981 | Brennan | 128/743 |
| 4,304,241 | 12/1981 | Brennan | 128/743 |

Primary Examiner—Lee S. Cohen
Assistant Examiner—Angela D. Sykes
Attorney, Agent, or Firm—Bachman and LaPointe

[57] ABSTRACT

A device for effecting multiple scarifications on spaced apart portions of a body has a rolling surface and a plurality of scarifiers extending outwardly of the rolling surface, in spaced relationship; the scarifiers sequentially penetrate the epidermis at spaced apart cutaneous sites when the rolling surface is rolled on the body part; in use the scarifiers support different freeze-dried allergen preparations on their outer scarifying ends.

22 Claims, 4 Drawing Figures

SKIN TESTING DEVICE

BACKGROUND OF THE INVENTION (a) Field of the Invention

The invention relates to a device for effecting multiple scarifications in the skin and more especially for effecting multiple skin tests in a single operation.

The invention also contemplates a method of effecting multiple skin tests sequentially.

(b) Description of the Prior Art

Skin tests are conducted as an essential part of medical diagnosis to determine materials that a patient may be allergic to.

The conventionally employed procedure is to place a drop of allergen in an aqueous medium to an appropriate site on the skin of the patient and to scratch the skin at the site with a scarifier so as to penetrate the epidermis to permit intracutaneous penetration of the allergen.

The performance of a large number of skin tests, sometimes as many as 50 different tests is a laborious, tedious, time consuming, uncomfortable and often traumatic experience for the patient, especially children.

It has previously been proposed to apply allergens in liquid form to a plurality of spaced apart sites on the skin and simultaneously to scarify the skin at such sites. U.S. Pat. No. 2,522,309—Frank A. Simon, U.S. Pat. No. 3,289,670—J. R. Krug et al and U.S. Pat. No. 3,556,080—Gary L. Hein.

The Simon and Krug et al devices comprise a plurality of scarifiers extending from a planar surface having a significant area and so the skin tests must necessarily be performed on a relatively large planar body portion such as the back, and this necessarily requires that the patient remove all upper garments to expose the back surface.

The Hein device also employs scarifiers which are all located in the same plane but the body of the device is generally "centipede shaped", and would seem costly to manufacture.

All three of these prior described devices require application of liquid allergen to the scarifiers and are relatively complex in structure or in any event are not designed as single use disposable items.

In addition the adherence of liquid allergens, particularly aqueous solutions, to the scarifiers, is difficult to achieve.

It is an object of the invention to provide a device which is simple in construction and overcomes the disadvantages of the prior devices.

It is a further object of the invention to provide such a device as a disposable item ready for a single use.

It is a further object of the invention to provide such a device which facilitates rapid multiple skin tests which may be conducted on any convenient skin area, including non-planar skin areas such as the upper arm and forearm.

It is yet another object of the invention to provide a method of effecting multiple skin tests, which can be performed rapidly with a minimum of inconvenience and discomfort to the patient.

SUMMARY OF THE INVENTION

In accordance with the invention a scarifying device has a rolling surface adapted to be rolled along or against a body portion, and a plurality of scarifiers extending outwardly from the rolling surface; and in particular the scarifiers suitably extend perpendicular to the rolling surface.

More particularly the invention provides a device for effecting multiple scarifications on spaced apart portions of a body comprising: a self-supporting body having a rolling surface and a plurality of scarifiers extending outwardly of said rolling surface, in spaced apart relationship, said scarifiers being adapted to sequentially penetrate the epidermis at spaced apart cutaneous sites when said rolling surface is rolled on said body part.

In one aspect of the invention, freeze-dried allergen is supported on the outer scarifying ends of the scarifiers. In particular each scarifier suitably supports a different freeze-dried allergen and a control scarifier supports no allergen at all or possibly may support nonallergenic material which may form part of the freeze-dried allergens on the other scarifiers.

It will be understood that the scarifiers having freeze-dried allergens are adapted to apply the allergenic material to the spaced apart sites, particularly to permit intracutaneous penetration of the allergen.

The invention also provides a disposable device for effecting multiple skin tests packaged in a sterile package and which is to be discarded after a single use which comprises: a self-supporting body having a rolling surface and a plurality of scarifiers extending outwardly from said surface in spaced apart relationship, a plurality of different freeze-dried allergenic preparations, each freeze-dried allergen being supported on an outer scarifying end of a scarifier, said body being sealed inside said package. In particular the scarifiers suitably extend perpendicular to the rolling surface.

Still further the invention provides a method of effecting multiple skin tests sequentially which comprises: rolling against a body part of self-supporting body having a rolling surface and a plurality of scarifiers extending outwardly of said surface in spaced apart relationship, said scarifiers supporting at their outer scarifying ends a plurality of different freeze-dried allergens so that said scarifiers sequentially penetrate the epidermis at spaced apart cutaneous sites and apply said allergen preparations to said spaced apart scarified cutaneous sites, and evaluating any reaction at said sites.

DESCRIPTION OF THE PREFERRED EMBODIMENTS

The self-supporting body may suitably be in the form of a wheel, the rolling surface being defined by the circumferential convexly curved surface of the wheel. On the other hand, the rolling surface need not define a surface of complete revolution as in the case of a surface defined by the circumference of a circle. It may be any curved surface, whether convexly curved or concavely curved which will provide a rolling action.

The scarifiers are suitably in the form of small tines having sharp points and which extend generally normal to or peripendicularly from the rolling surface.

The scarifiers are all substantially identical and are spaced apart on the rolling surface so as to provide an appropriate spacing of the individual test sites, so as to avoid interference between adjacent sites and permit proper identification and evaluation of the different test sites.

The body, including the scarifiers, are relatively rigid or self-supporting and in particular the scarifiers must be sufficiently rigid to achieve their scarifying function. Preferably the scarifiers should be sufficiently rigid that they have no significant flexure during the scarification such as would result in any substantial lateral movement of the scarifier relative to the skin.

The body and scarifiers are suitably formed of metal or a plastic material which can be readily sterilized.

In particular the body with the outwardly extending scarifiers may be molded as a unitary component from a plastic material, and this provides a device which can be economically produced as a disposable item intended for a single use.

Different aqueous allergenic preparations can be freeze-dried on the individual scarifiers by known techniques.

BRIEF DESCRIPTION OF THE DRAWINGS

Particular embodiments of the invention are illustrated with reference to the accompanying drawings in which.

DESCRIPTION OF THE PREFERRED EMBODIMENTS WITH REFERENCE TO THE DRAWINGS

Figure 1:
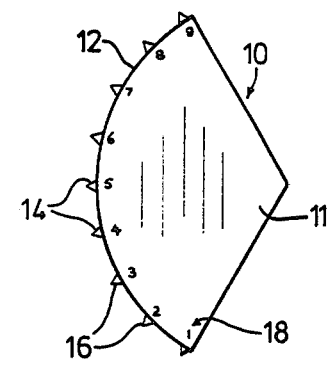
FIG. 1 is a perspective view of one embodiment of a device of the invention.

With reference to FIG. 1, a skin test device 10 includes a body portion 11 and a roller surface 12.

A plurality of scarifiers 14 extend normal to the surface 12 in spaced apart relationship. The outer scarifying ends of the scarifiers 14 support different freeze-dried allergens 16.

Identifying integers 18 are disposed on body portion 11 along side the scarifiers 14. Each integer 18 is associated with a scarifier 14 having a particular freeze-dried allergen preparation 16 thereon.

The device 10 can suitably be molded from plastic material as a unitary article and the preparation 16 can be freeze-dried on the scarifiers 14 by known techniques.

In the manufacture of device 10 a particular allergen 16 is associated with each identifying integer 18.

The device 10 is suitably supplied sealed in an envelope effective to support a sterile environment for device 10. For example, it may be packaged in a cellophane envelope which is sealed, the package and its contents being sterilized by ultraviolet light.

In order to carry out the skin test the medical practitioner first removes device 10 from its sealed envelope. Device 10 is suitably held between the thumb and forefinger by body portion 11 and the roller surface 12 is rotated against the skin of the patient so that the lowermost scarifier 14, shown in FIG. 1, being the scarifier 14 associated with integer number 1 of the identifying integers 18, is the first of the scarifiers 14 to penetrate the epidermis of the skin, whereafter the scarifiers 14 associated with integer numbers 2, 3, 4, etc. sequentially penetrate the epidermis.

The reaction of the skin to the allergen, if any, is then evaluated in the usual way, within an appropriate period, usually about 15 minutes, after the scarifying operation.

Typically one of the scarifiers 14 will have no freeze-dried allergen, and this serves as a comparison or control.

After use the device 10 can be discarded.

Figure 2:
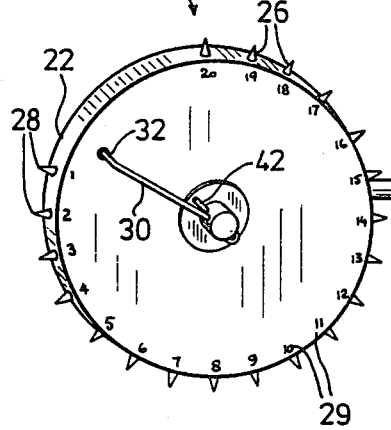
FIG. 2 is a side view of a device in a different embodiment of the invention.
Figure 3:
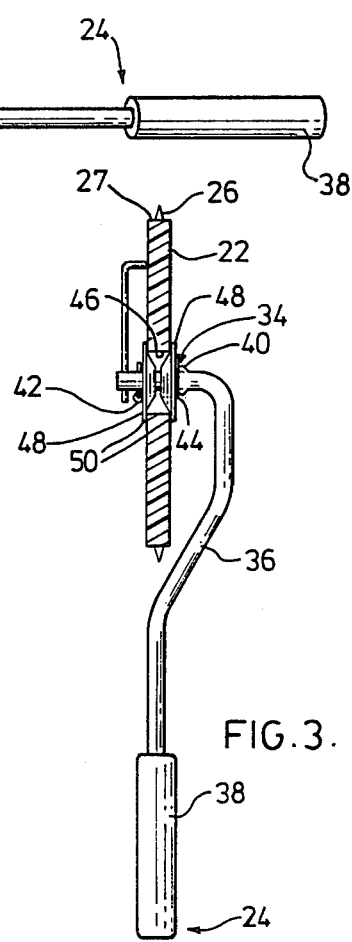
FIG. 3 is an end view of the device shown in FIG. 2.

With further reference to FIGS. 2 and 3, a skin test device 20 includes a wheel or disc 22 and a handle member 24.

Wheel 22 includes a plurality of spaced apart scarifiers 26 extending normal to the circumferential curved surface 27.

The scarifiers 26 have different freeze-dried allergenic preparations 28 on an outer scarifying end thereof, one of the scarifiers 26 being free of allergen preparation and serving as a control.

Identifying integers 29 are associated with the scarifiers 26 in a manner similar to that described for device 10 in FIG. 1.

Wheel 22 further includes a recess 32 and a spindle bore 46, the purpose of which is indicated below.

Handle member 24 includes a spindle 34, a handle bar 36 and a handle element 38.

A stop 40 is disposed at the juncture of spindle 34 and handle bar 36.

Spindle 34 is adapted to pass centrally of spindle bore 46.

Spindle 34 is mounted within spindle bore 46 in a pair of spaced apart dish-shaped members 48 which sit in the opposed openings of spindle bore 46.

Each of dish-shaped members 48 has a retaining flange 50 which serves to seat dish-shaped members at opposed ends of spindle bore 46.

A washer 44 is disposed over spindle 34 between stop 40 and the adjacent dish-shaped member 48.

Spring nut 42 on spindle 34 secures the assembly together for rotation of wheel 22 with members 48 on spindle 34.

At the outermost end of spindle 34 is an L-shaped locking member 30, the long arm of the L-shaped member being snugly but rotatably seated in a bore passing perpendicularly to the axis of spindle 34.

In the locking position, the short arm of the L-shaped locking member 30 engages the recess 32 in wheel 22.

The device 20 can be molded of plastic in much the same way as device 10 illustrated in FIG. 1, and can suitably be provided in a sterile package ready for mounting on handle member 24.

It will be recognized that handle member 24 is merely exemplary of one means of supporting wheel 22 for rotation.

Handle member 24 and its accessories may suitably be of metal which can be readily sterilized. Of course, in this case, wheel 22 is the sole disposable part of the device 20, handle member 24 and its accessories being reusable.

Locking member 30 locks wheel 22 in position such that the scarifier 26 associated with integer number 1 of the identifying integers 29 is always in the position to be the first of the scarifiers 26 to penetrate the epidermis, with the scarifiers 26 associated with integers 2, 3, 4, etc. of the identifying integers 18 penetrating the epidermis sequentially in spaced apart positions during the scarifying operation.

In order to carry out the scarifying operation the wheel 22 is placed in contact with the skin such that the integer 26 associated with integer number 1 contacts the skin, the locking member 30 is released by turning it so that a short arm of the L leaves recess 32, whereafter the wheel 22 is rolled along the skin in one brief movement.

In order to roll wheel 22 the user holds the device 20 by means of handle element 38 and urges wheel 22 with a rolling action against the skin such that the scarifiers 26 penetrate the epidermis sequentially, suitably to a depth of about 1 mm, and the different freeze-dried preparations 28 penetrate the epidermis.

After completion of the scarifying operation the device 20 is dissembled and wheel 20 can be discarded and replaced with a fresh wheel 20, with a different set of allergen preparations 28 for conducting further skin tests on the same patient, or with a similar wheel for carrying out the same tests on a different patient.

Figure 4:
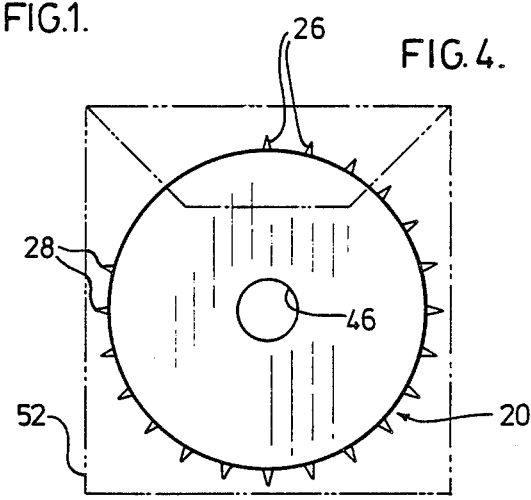
FIG. 4 shows a packaged device.

With further reference to FIG. 4 there is shown a wheel or disc 22 of FIG. 2 sealed in an envelope 52.

Conveniently the scarifiers are spaced apart on the rolling surface at equal intervals.

A variety of freeze-dried allergenic substances may be employed as will be readily understood in freeze-dried form including grass, tree and shrub preparations, preparations based on pollens, fungi and other inhalant substances, food and bacteria, animal hair, molds, cotton, wool, silk, etc.

It is also useful in the diagnosis and determination of the causes of bronchial asthma, hay fever, eczema, urticaria, gastrointestinal allergies and other allergic conditions.

The individual devices sealed in envelopes may be supplied in a dispenser, which function to store them prior to use, and from which they can be removed as needed.

I claim:

1. A device for effecting multiple scarifications on spaced apart portions of a body comprising:
   a self-supporting body having a convexly curved rolling surface and a plurality of scarifiers extending outwardly of said rolling surface, in spaced apart relationship, said scarifiers having outer scarifying ends,
   said rolling surface being adapted to be rolled on a body portion for sequential penetration of the epidermis at spaced apart cutaneous sites, by said scarifying ends.

2. A device according to claim 1, wherein said scarifiers support different freeze-dried allergen preparations on their outer scarifying ends.

3. A device according to claim 2, wherein one of said scarifiers is a control scarifier and is free of allergen preparation.

4. A device according to claim 3, including identifying data on said self-supporting body associated with said scarifiers, such that the control scarifier and the different allergen preparations are readily identifiable.

5. A device according to claim 4, wherein said body is in the form of a wheel.

6. A device according to claim 2, wherein said rolling surface is defined by at least part of a cylindrical surface.

7. A device according to claim 6, wherein said self-supporting body is in the form of a wheel.

8. A device according to claim 1, wherein said scarifiers extend normal to said rolling surface.

9. A disposable device for effecting multiple skin tests packaged in a sterile package and which is to be discarded after a single use, comprising:
   a self-supporting body having a convexly curved rolling surface and a plurality of scarifiers extending outwardly of said surface in spaced apart relationship, said scarifiers having outer scarifying ends,
   said rolling surface being adapted to be rolled on a body portion for sequential penetration of the epidermis at spaced apart cutaneous sites, by said scarifying ends,
   a plurality of different freeze-dried allergen preparations supported on the outer scarifying ends,
   said body being sealed inside said package.

10. A packaged device according to claim 9, wherein said device is individually packaged.

11. A packaged device according to claim 9, wherein one of said scarifiers is a control scarifier and is free of allergen preparation.

12. A packaged device according to claim 11, including identifying data on said body associated with said scarifiers, such that the control scarifier and the different allergen preparations are readily identifiable.

13. A packaged device according to claim 12, wherein said body is in the form of a wheel.

14. A packaged device according to claim 9, wherein said body is in the form of a wheel.

15. An assembly for effective multiple skin tests on spaced apart portions of a body part comprising:
   a wheel-shaped member having a circumferential curved surface, said wheel-shaped member adapted to be rolled on said body portion,
   a plurality of scarifiers extending outwardly of the circumferential curved surface of said wheel-shaped member, in spaced apart relationship, said scarifiers having outer scarifying ends,
   a handle element including a spindle, and means for temporarily mounting said wheel-shaped member for rotation about said spindle,
   a plurality of different freeze-dried allergen preparations supported on the outer scarifying ends,
   said scarifiers being adapted to sequentially penetrate the epidermis at spaced apart cutaneous sites when said curved surface is rolled along said body part, and to apply said different freeze-dried allergen preparations to the sites.

16. An assembly according to claim 15, wherein said scarifiers extend normal to said curved surface.

17. An assembly according to claim 16, wherein one of said scarifiers is a control scarifier and is free of allergen preparation.

18. An assembly according to claim 17, including identifying data on said wheel-shaped member associated with said scarifiers, such that the control scarifier and the different allergen preparations are readily identifiable.

19. A method of effecting multiple skin tests sequentially which comprises:
   rolling against a body part a self-supporting body having a convexly curved rolling surface and a plurality of scarifiers extending outwardly of said surface in spaced apart relationship, said scarifiers having outer scarifying ends and supporting at said ends a plurality of different freeze-dried allergen preparations so that said scarifiers sequentially penetrate the epidermis at spaced apart cutaneous sites,
   applying said allergen preparations to said spaced apart scarified cutaneous sites,
   and evaluating any reaction at said sites.

20. A method according to claim 19, wherein said body is in the form of a wheel.

21. A method according to claim 20, wherein one of said scarifiers is a control scarifier and is free of allergen preparations.

22. A method according to claim 21, wherein said body comprises identifying data associated with said scarifiers, such that the control scarifier and the different allergen preparations are readily identifiable.

* * * * *